United States Patent [19]

Glowacki et al.

[11] 4,440,750

[45] Apr. 3, 1984

[54] OSTEOGENIC COMPOSITION AND METHOD

[75] Inventors: Julianne Glowacki, Jamaica Plain, Mass.; Bruce B. Pharriss, Palo Alto, Calif.

[73] Assignees: Collagen Corporation, Palo Alto, Calif.; President and Fellows of Harvard College, Cambridge, Mass.

[21] Appl. No.: 348,414

[22] Filed: Feb. 12, 1982

[51] Int. Cl.$^3$ ...................... A61K 35/32; A61K 37/00
[52] U.S. Cl. ........................................ 424/95; 424/177
[58] Field of Search ................................ 424/95, 177

[56] References Cited

U.S. PATENT DOCUMENTS 3,443,261 5/1969 Battista et al. .
3,458,397 7/1969 Myers et al. .
3,949,073 4/1976 Daniels et al. .
4,191,747 3/1980 Scheicher .

OTHER PUBLICATIONS

Werner et al.–Chem. Abst. vol. 93 (1980) p. 225, 666S.
"Induced Osteogenesis for Repair and Construction in the Craniofacial Region" Mulliken, J. B. and Glowacki, Jr. Plastic and Reconstructive Surgery, May 1980, pp. 553–559.

*Primary Examiner*—Sam Rosen
*Attorney, Agent, or Firm*—Ciotti & Murashige

[57] ABSTRACT

A plastic dispersion of demineralized bone powder and reconstituted native atelopeptide collagen fibers in a continuous aqueous phase having a substantially physiologic pH and ionic strength is used to repair or construct bone by injecting or implanting it at the repair or construction site. Once emplaced the dispersion induces rapid and complete osteogenesis at the site.

18 Claims, No Drawings

OSTEOGENIC COMPOSITION AND METHOD

DESCRIPTION

1. Technical Field

The invention relates to an osteogenic composition that may be used to repair or construct bone.

2. Background Art

A wide variety of materials have been used to replace or repair bone including bone segments, bone powder, bone paste, and bone derivatives such as demineralized bone. "Induced Osteogenesis for Repair and Construction in the Craniofacial Region" Mulliken, J. B. and Glowacki, J. Plastic and Reconstructive Surgery, May 1980, pp 553–559, provides an historical review of natural materials that have been used in craniofacial bone grafting. The article reports comparative experiments involving fresh bone segment, fresh bone paste, devitalized bone powder, demineralized bone segments, and demineralized bone powder. The demineralized bone powder was found to be osteogenic.

U.S. Pat. No. 3,458,397 describes an osteogenic material made by proteolytically digesting bone, separating the liquid from the solid, forming a precipitate from the liquid by adding acetone or an alcohol, and drying the precipitate.

U.S. Pat. No. 3,443,261 discloses a composition made from a solution of a collagen salt and calcium phosphate that dries to cartilage-like or bone-like products.

U.S. Pat. No. 4,191,747 concerns a composition for covering or filling bone defects that consists of a solution of a polysaccharide and/or gelatin in physiological saline solution which gels at physiological temperature. The composition is reabsorbed or dissolves during or after osteogenesis. Ions such as alkali metal ions that stimulate bone growth and substantial amounts of denatured bone meal may be included in the composition.

Atelopeptide collagen in solution has been used for augmenting soft, connective tissue. U.S. Pat. No. 3,949,073 describes the preparation and administration of such a solution. The solution is typically administered by injection. Once applied to the augmentation site, it reconstitutes into a fibrous tissue mass that is rapidly colonized by host cells and revascularized.

A main object of the invention is to provide an osteogenic composition that is malleable under the conditions of administration and induces rapid and complete osteogenesis at the administration site.

DISCLOSURE OF THE INVENTION

One aspect of the invention is an osteogenic composition comprising a plastic dispersion of particulate demineralized bone and reconstituted collagen fibers in a continuous aqueous phase having a substantially physiological pH and ionic strength.

A second aspect of the invention is a method for inducing osteogenesis at a site within a living vertebrate comprising emplacing the above-mentioned dispersion at said site.

MODES FOR CARRYING OUT THE INVENTION

Particulate demineralized bone and reconstituted collagen are the two principal components of the composition. The collagen used in the invention is atelopeptide collagen or tropocollagen and may typically be collected from any number of mammalian sources. Atelopeptide collagen is preferred. The donor need not be genetically similar to the host in which the collagen is ultimately emplaced. Because of their availability, bovine or porcine corium will usually be the source of the collagen used in the invention.

The first step in preparing atelopeptide collagen from animal skin is to soften the skin by soaking it in a mild acid and then scraping it to remove hair, epidermis, and fat. The depilated skin is then soaked again in mild acid and then comminuted by grinding, mincing, milling or like physical treatment. The comminution prepares the skin for solubilization. The divided tissue may be solubilized under nondenaturing conditions by dispersing it in an aqueous acid medium and digesting it with a proteolytic enzyme other than a collagenase. Dilute acid solution at low temperatures will normally be used to avoid denaturation. Mineral acids such as HCl or carboxylic acids such as acetic, malonic or lactic acids may be used at pHs in the range of about 1.5 to 5 and temperatures of about 5° C. to 25° C. A preferred procedure is to disperse the comminuted tissue in HCl to a concentration of 1 to 5 g/l at a pH of about 2° to 20° C. After the tissue is dispersed the enzyme is added and the mixture is incubated to permit the enzyme to digest the telopeptide and other solubilizable components of the tissue. Enzymes that attack the telopeptide portion of the collagen while not denaturing its helical portion are used. Examples of such enzymes are trypsin, pepsin, chymotrypsin, and papain. Pepsin is preferred because it is relatively easily deactivated and removed from the solubilized collagen. The enzyme concentration will usually be in the range of about 0.1% to 10% by weight based on the collagen. The incubation period will typically vary from about two days to two weeks. The progress of the solubilization may be monitored by determining the viscosity of the solution. Once the viscosity reaches a substantially constant level, the solubilization is complete. At this point, the enzyme is deactivated (denatured) and removed.

The enzyme may be deactivated by raising the pH of the solution to at least about 7 by adding an alkaline material such as sodium hydroxide. After the enzyme has been denatured the solution is treated to remove denatured enzyme and the portions of the tissue that were digested during the solubilization. Various dialysis, sedimentation, and filtration techniques may be used to effect such removal. See U.S. Pat. Nos. 3,949,073 col. 3, lines 10–22 and 4,140,537 col. 5, line 48 to col. 6 line 34, which disclosures are incorporated herein by reference. A preferred procedure is to first lower the pH by adding acid and then clarify the solution by diatomaceous earth sedimentation. The sediment is filtered and the filtrate is concentrated. The concentrate is then purified by ion exchange and further concentrated. The resulting substantially pure atelopeptide collagen solution may be sterilized by dialysis, irradiation, filtration, or chemical treatment. Filtration is a preferred sterilization procedure. After sterilization the collagen may be left in solution pending reconstitution and formulation with the particulate demineralized bone or it may be reconstituted promptly. It is reconstituted by increasing the pH of the solution to above about 7. This is preferably accomplished by adding $Na_2HPO_4$ to the solution. The precipitated collagen is then separated from the supernatant and then dispersed in an aqueous medium at physiological pH (6.8 to 7.5) and ionic strength (0.1 to 0.2), typically at concentrations of 20 to 100 mg/ml.

Tropocollagen may be prepared in a similar way but without enzyme treatment to remove telopeptides. The tropocollagen may be reaggregated into fibers in the same manner as atelopeptide collagen.

The bone that is used in the invention may also typically be collected from a variety of mammalian sources. Homogeneic and xenogeneic sources may be used. Bovine and porcine bone, preferably long bone, will normally be used because of its availability. The surface of the bone is first cleaned by physically removing periosteum by scraping or brushing. The bone is then fragmented into small pieces and the fragments are water washed with agitation to remove any water soluble materials remaining on the fragments. The washing is preferably carried out at reduced temperatures, usually about 5° C. to 18° C., with frequent changing of the wash water. The fragments are then dried, extracted with one or more lipophilic solvents, such as ethanol and ethyl acetate, to remove lipids and dehydrate the bone. The fragments are then dried under vacuum and comminuted by crushing, milling or pulverizing, preferably at reduced temperatures to increase the friability of the bone. The bone is accordingly converted into a finely divided powder having a particle size in the range of about 25 to 1000 microns, preferably 75 to 250 microns. Division of the bone into small particles facilitates extracting the minerals from it and increases the volume fraction of induced bone formation.

The principal mineral component of bone is calcium phosphate. The term "calcium phosphate" as used herein is intended to encompass the numerous calcium-phosphorus complexes and compounds present in bone such as the various polycalcium phosphates, hydroxyapatite, chlorapatite, and the like. Calcium phosphate usually constitutes about 80% of the mineral content of bone. Other mineral components of bone include calcium carbonate, calcium fluoride, calcium chloride, and magnesium phosphate. These minerals are normally soluble in dilute mineral and organic acids and such acids may be used to demineralize bone. The concentration of the acid used to demineralize the bone will usually be between 0.1 M to 1.0 M. Hydrochloric acid at a concentration of 0.5 M is preferred. The bone will normally be contacted with the acid for one hour to several days at temperatures ranging from about 5° C. to about 22° C. Agitation will facilitate extraction of the minerals from the bone. After the extraction is complete the bone is separated from the acid such as by sedimentation, filtration or other conventional solid-liquid separation techniques and the bone is washed with water, ethanol, and ether to remove adsorbed acid and dehydrate it. The dried bone may be sterilized by irradiation, ethylene oxide treatment, or other known solids sterilization methods.

The bone and collagen may either be stored separately pending use or mixed and packaged as an integral step in the manufacture of the osteogenic composition. Preferably they are mixed and packaged as an integral step in the composition manufacture. The two components are mixed together under sterile conditions in the desired proportions. The collagen will usually constitute about 30% to 90% by weight of the dispersed phase whereas the demineralized bone will usually constitute 10% to 70% by weight of the dispersed phase. Preferably the collagen constitutes 40% to 50% by weight of the dispersed phase and the demineralized bone constitutes 50% to 60% by weight of the dispersed phase. The total solids (bone and collagen combined) will usually constitute about 20% to about 60% by weight of the dispersion, preferably 30% to 50% by weight. Minor amounts of additives such as surfactants, salts, buffers, drugs such as immunosuppressants, anesthetics, antibiotics and hemostats, angiogenesis factors, fibroblast growth factors and bone growth stimulants such as those disclosed in U.S. Pat. No. 4,191,747 at col. 3, line 50 to col. 4, line 13, which disclosure is incorporated herein by reference, may be added to the bone and collagen at the time of mixing. The compositions may be fluid or nonfluid depending upon the concentrations of demiineralized bone and collagen fibers. Fluid forms of the composition, which include gels, will usually have viscosities below about 50,000 cp at 37° C., whereas the nonfluids will usually have viscosities above that magnitude. Injectable fluid forms of the composition may be packaged directly injection devices such as syringes. Forms of the osteogenic composition that are substantially nonfluid may be packaged in dispensers that are commonly used to dispense paste or ointments. The packaged compositions are preferably stored at reduced temperatures, usually 0° C. to 25° C., pending their administration to the patient.

The injectable forms of the composition are injected into the site at which bone formation is desired, whereas the nonfluid forms will be surgically implanted at such sites. Common sites typically are in the vicinity of existing bone, either supra or subperiosteally, or surrounding fracture or graft fragments, but are not restricted to presently ossified regions. These compositions may be used to correct congenital, acquired, or cosmetic bone defects. They are especially advantageous as compared to fresh bone segments or bone powder since they are plastic and cohesive and may be readily deformed to fit the size and contour of the administration site. The ability to form the composition to fit the site exactly is especially important in osteoplastic uses of the composition as well as in filling fractures to promote fusion. Osteogenesis is coextensive with the entire mass or volume of the implant, thus making it possible to control the size and shape of the new bone.

Bone induction at the implant site proceeds generally by deposition of cartilage in the interstices between demineralized bone particles, which then is converted to bone by endochondral osteogenesis similar to normal growth and fracture healing processes. Depending on the site of implantation, the cells responsible for cartilage and bone formation may already have osteogenic competence at the time of migration into the implant, or they may be undifferentiated mesenchymal or fibroblastic cells from nonbone tissue, which take on an osteogenic phenotype on contact with an inducing factor bound to or diffusing from the demineralized matrix. Other cell types may migrate into the implant, such as mast cells and macrophages, but do not interfere with the induction process unless present in excessive number. Blood vessels do not normally appear during the cartilage phase of bone growth, but occur during bone deposition, remodeling and later colonization of the induced bone by hematopoietic marrow cells. The function of the collagen gel surrounding the demineralized bone particles is to provide a substrate for rapid migration of osteogenic cells and blood vessels.

The following example further illustrates the invention. This example is not intended to limit the invention in any manner. Unless indicated otherwise, percentages are given by weight.

The materials and methods used are as follows:

ATELOPEPTIDE COLLAGEN

ZYDERM collagen (Collagen Corp., Palo Alto, CA) is used. This material is made from fresh bovine corium that is digested with pepsin and purified. The collagen fibers are suspended in an aqueous medium of physiological pH and ionic strenth at a concentration of 35 mg/ml.

DEMINERALIZED BONE POWDER

Fresh bovine femur is brushed to remove periosteum and then fragmented into pieces less than 0.5 cm largest dimension. The fragments are washed in water at 5° C. with agitation for one day with frequent change of the wash water. The fragments are then extracted at room temperature three times with 95% ethanol for 20 minutes each time. The volume of ethanol in each extraction is triple the volume of bone. The fragments are then dried under vacuum at ambient temperature and then extracted three times with ethyl acetate. Each extraction is made for 20 min. The ethyl acetate volume is triple the bone volume. The fragments are again dried under vacuum and are then pulverized in a liquid nitrogen mill. The pulverized powder is sieved and the 75–450 micron portion is recovered. That portion is extracted with 0.5 N HCl at room temperature for three hours. The volume of HCl is ten fold the bone volume. Following the HCl extraction the pulverized bone is washed until the pH of the wash liquid reached 5. The triple ethanol and ethyl acetate extractions are then repeated.

METHODS

The demineralized bone powder is hydrated with physiological saline to form a paste-like suspension containing 500 mg bone/ml saline. This suspension is mixed with the atelopeptide collagen fiber preparation such that the weight ratio of bone to collagen in the resulting aqueous dispersion is 1:1. This dispersion is loaded into a syringe and may be injected into a living vertebrate such as a human, a domestic, pet, or sport animal to induce bone formation at the site of its implantation.

Modifications of the above described modes for carrying out the invention that are obvious to those of ordinary skill in the chemical and/or medical arts are intended to be within the scope of the following claims.

We claim:

1. An osteogenic composition comprising a plastic dispersion of particulate demineralized bone and reconstituted collagen fibers dispersed in a continuous aqueous phase having a substantially physiological pH and ionic strength.

2. The osteogenic composition of claim 1 wherein the collagen is atelopeptide collagen.

3. The osteogenic composition of claim 1 or 2 wherein the demineralized bone constitutes about 10% to about 70% by weight of the dispersed phase and the reconstituted collagen fibers constitute about 30% to about 90% by weight of the dispersed phase.

4. The osteogenic composition of claim 1, 2 or 3 wherein the demineralized bone has a particle size in the range of about 25 to about 1000 microns.

5. The osteogenic composition of claim 1 or 2 wherein the demineralized bone has a particle size in the range of 75 to 250 microns.

6. The osteogenic composition of claim 1 or 2 wherein the dispersed phase constitutes about 20% to about 60% by weight of the dispersion.

7. The composition of claim 1 or 2 wherein the pH is in the range of 6.8 to 7.5 and the ionic strength is in the range of 0.1 to 0.2.

8. The composition of claim 1 or 2 wherein the source of the demineralized bone is bovine long bone and the source of the collagen is bovine corium.

9. The osteogenic composition of claim 1 wherein the plastic dispersion is in the form of an injectable fluid.

10. The osteogenic composition of claim 1 wherein the plastic dispersion is in the form of a substantially nonfluid semisolid.

11. A method for inducing osteogenesis at a site within a living vertebrate comprising emplacing a plastic dispersion of particulate demineralized bone and reconstituted collagen fibers in a continuous aqueous phase having a substantially physiological pH and ionic strength at said site.

12. The method of claim 11 wherein the demineralized bone powder constitutes about 10% to about 70% by weight of the dispersed phase and the reconstituted collagen fibers constitute about 30% to about 90% by weight of the dispersed phase and the dispersed phase constitutes about 20% to about 60% by weight of the dispersion.

13. The method of claim 11 or 12 wherein the collagen is atelopeptide collagen.

14. The method of claim 13 wherein the demineralized bone has a particle size in the range of about 75 to 250 microns.

15. The method of claim 13 wherein the pH is in the range of 6.8 to 7.5 and the ionic strength is in the range of 0.1 to 0.2.

16. The method of claim 13 wherein the vertebrate is a human and the sources of the bone and the collagen are xenogeneic.

17. The method of claim 13 wherein the plastic dispersion is in the form of an injectable fluid and the emplacement of the dispersion is effected by injection.

18. The method of claim 13 wherein the plastic dispersion is in the form of a substantially nonfluid semisolid and the emplacement of the dispersion is effected by surgical implantation.

* * * * *